(12) United States Patent
Suh

(10) Patent No.: US 11,419,732 B2
(45) Date of Patent: Aug. 23, 2022

(54) FLEXIBLE ANCHORING AND FUSION DEVICES AND METHODS OF USING THE SAME

(71) Applicant: GLOBUS MEDICAL, INC., Audubon, PA (US)

(72) Inventor: Sean Suh, Morganville, NJ (US)

(73) Assignee: Globus Medical Inc., Audubon, PA (US)

( * ) Notice: Subject to any disclaimer, the term of this patent is extended or adjusted under 35 U.S.C. 154(b) by 233 days.

(21) Appl. No.: 15/784,658

(22) Filed: Oct. 16, 2017

(65) Prior Publication Data

US 2018/0036133 A1 Feb. 8, 2018

Related U.S. Application Data

(60) Continuation of application No. 14/967,588, filed on Dec. 14, 2015, now Pat. No. 9,814,591, which is a division of application No. 13/245,139, filed on Sep. 26, 2011, now Pat. No. 9,241,806.

(51) Int. Cl.
*A61F 2/44* (2006.01)
*A61F 2/46* (2006.01)
*A61B 17/86* (2006.01)
*A61F 2/30* (2006.01)

(52) U.S. Cl.
CPC .......... *A61F 2/441* (2013.01); *A61B 17/864* (2013.01); *A61B 17/8625* (2013.01); *A61F 2/447* (2013.01); *A61F 2/4611* (2013.01); *A61F 2002/30014* (2013.01); *A61F 2002/30092* (2013.01); *A61F 2002/30136* (2013.01); *A61F 2002/30354* (2013.01); *A61F 2002/30406* (2013.01); *A61F 2002/30583* (2013.01); *A61F 2002/30774* (2013.01); *A61F 2002/30779* (2013.01); *A61F 2002/30886* (2013.01); *A61F 2002/30891* (2013.01); *A61F 2002/448* (2013.01); *A61F 2002/449* (2013.01); *A61F 2002/4638* (2013.01); *A61F 2310/00017* (2013.01); *A61F 2310/00023* (2013.01); *A61F 2310/00029* (2013.01)

(58) Field of Classification Search
CPC .......................... A61B 1/0058; A61B 17/1642
See application file for complete search history.

(56) References Cited

U.S. PATENT DOCUMENTS

| 4,601,705 A | * | 7/1986 | McCoy | A61B 1/0051 600/151 |
|---|---|---|---|---|
| 5,549,679 A | | 8/1996 | Kuslich | |
| 5,954,722 A | | 9/1999 | Bono | |
| 6,053,922 A | | 4/2000 | Krause et al. | |

(Continued)

*Primary Examiner* — Jan Christopher L Merene

(57) ABSTRACT

A spacer member is provided that is configured to be implanted adjacent an anatomical structure. The spacer member defines a curved bore, a first opening in a side wall of the spacer member and a second opening in one of a top wall and a bottom wall of the spacer member. Each of the first opening and the second opening are in fluid communication with the curved bore. A flexible anchoring member is configured to be inserted through the side opening and through the curved bore of the spacer member such that a distal end portion of the flexible anchoring member extends out of the second opening at an angle relative to the one of the top wall and the bottom wall of the spacer member.

12 Claims, 13 Drawing Sheets

(56) References Cited

U.S. PATENT DOCUMENTS

| | | |
|---|---|---|
| 6,206,881 B1 | 3/2001 | Frigg et al. |
| 6,447,546 B1 | 9/2002 | Bramlet et al. |
| 6,629,998 B1 | 10/2003 | Lin |
| 7,077,864 B2 | 7/2006 | Byrd et al. |
| 7,534,268 B2 | 5/2009 | Hudgins et al. |
| 7,744,630 B2 | 6/2010 | Lancial |
| 7,892,261 B2 | 2/2011 | Bonutti |
| 8,313,528 B1 | 11/2012 | Wensel |
| 8,523,945 B1 | 9/2013 | Wensel |
| 8,551,175 B1 | 10/2013 | Wensel |
| 2002/0183758 A1* | 12/2002 | Middleton ......... A61B 17/1664 606/79 |
| 2003/0225364 A1* | 12/2003 | Kraft .................. A61B 10/025 604/35 |
| 2004/0073218 A1 | 4/2004 | Dahners |
| 2004/0092933 A1* | 5/2004 | Shaolian ........ A61B 17/320016 606/279 |
| 2004/0162559 A1* | 8/2004 | Arramon ............ A61B 17/3417 606/62 |
| 2004/0193162 A1 | 9/2004 | Bramlet et al. |
| 2005/0070904 A1 | 3/2005 | Gerlach et al. |
| 2005/0240201 A1* | 10/2005 | Yeung ................ A61B 17/7061 606/108 |
| 2006/0241593 A1 | 10/2006 | Sherman et al. |
| 2007/0225721 A1* | 9/2007 | Thelen .............. A61B 17/1668 606/80 |
| 2008/0051793 A1* | 2/2008 | Erickson ........... A61B 17/1671 606/279 |
| 2008/0177294 A1* | 7/2008 | O'Neil ............... A61B 17/1659 606/167 |
| 2009/0105832 A1 | 4/2009 | Allain et al. |
| 2009/0118771 A1 | 5/2009 | Gonzalez-Hernandez |
| 2010/0292695 A1 | 11/2010 | May et al. |
| 2010/0312345 A1 | 12/2010 | Duffield et al. |
| 2011/0015682 A1 | 1/2011 | Lewis et al. |
| 2011/0106157 A1 | 5/2011 | Melkent et al. |
| 2011/0144703 A1* | 6/2011 | Krause ................ A61B 17/869 606/309 |
| 2011/0230971 A1 | 9/2011 | Donner et al. |
| 2011/0282387 A1 | 11/2011 | Suh et al. |
| 2012/0078373 A1 | 3/2012 | Gamache et al. |
| 2012/0129676 A1* | 5/2012 | Duffy .................. A61B 10/025 494/37 |
| 2012/0232599 A1 | 9/2012 | Schoenly et al. |
| 2012/0245585 A1* | 9/2012 | Kaiser ................ A61B 17/1633 606/80 |
| 2012/0277582 A1* | 11/2012 | Mafi ................... A61B 5/6858 600/431 |
| 2013/0023876 A1 | 1/2013 | Rabiner |
| 2013/0150968 A1 | 6/2013 | Dinville et al. |
| 2013/0190874 A1 | 7/2013 | Glazer |
| 2013/0245767 A1 | 9/2013 | Lee et al. |
| 2015/0066033 A1* | 3/2015 | Jorgensen ......... A61B 17/1615 606/79 |

* cited by examiner

FLEXIBLE ANCHORING AND FUSION DEVICES AND METHODS OF USING THE SAME

CROSS REFERENCE TO RELATED APPLICATIONS

The present application is a continuation application of U.S. patent application Ser. No. 14/967,588, filed Dec. 14, 2015, which is a divisional application of U.S. patent application Ser. No. 13/245,139 filed on Sep. 26, 2011, entitled "Flexible Anchoring and Fusion Devices and Methods of Using the Same", now U.S. Pat. No. 9,241,806, the entire contents of which are incorporated herein by reference.

TECHNICAL FIELD

This disclosure relates generally to implants and more particularly to anchoring devices configured to be coupled to a portion of a spine and a flexible medical tool that can be used to form a curved path within a portion of a spine.

BACKGROUND

A variety of implants and implant systems are implanted within a body of a patient to provide support to a portion or portions of the patient's body. For example, some implants are implanted and coupled to backbones or portions of a spine of a patient and are configured to provide support to the spinal bone structure of the patient. Some implant systems that are configured to provide support to the spinal bone structure of a patient include support members or fusion rods that are implanted within an interior portion of the spinal bone structure, such as, within an intervertebral disc and/or within a vertebra. Some implants are configured to be secured to a spinal bone structure with, for example, an anchoring fastener, such as, an anchoring screw.

In some cases, access to implant or insert such support devices and/or anchoring devices within a body structure of a patient can be challenging. Typical linear and/or rigid support and anchoring devices are inserted along a straight path and access can be limited. It can also be difficult to avoid breaching neighboring anatomy when inserting the anchoring device. In addition, typical medical tools configured to drill or form a path or bore within a body structure to receive such support and anchoring devices are also rigid and can only form a straight or linear bore or passageway.

Accordingly, there is a need for medical support devices and anchoring devices that are flexible and can be inserted along a curved trajectory or bore within a body structure. There is also a need for medical boring or drilling devices that are flexible and can form a curved passageway or bore within a body structure that can receive a curved support device or anchoring device.

SUMMARY

In some embodiment, an implant includes, a spacer member configured to be implanted adjacent an anatomical structure. The spacer member defines a curved bore, a first opening in a side wall of the spacer member and a second opening in one of a top wall and a bottom wall of the spacer member. Each of the first opening and the second opening are in fluid communication with the curved bore. A flexible anchoring member is configured to be inserted through the side opening and through the curved bore of the spacer member such that a distal end portion of the flexible anchoring member extends out of the second opening at an angle relative to the one of the top wall and the bottom wall of the spacer member.

In some embodiments, an implant includes an expandable fusion member configured to be inserted while in a collapsed configuration into a portion of a first vertebra of a patient. The expandable fusion member is configured to receive an inflation medium within an interior region defined by the expandable fusion member to move the expandable fusion member from the collapsed configuration to an expanded configuration while disposed within the first vertebra. When in the expanded configuration, the first portion of the expandable fusion member extends within a bore within a first portion of a vertebra, and the second portion extends within a second bore within the first vertebra.

In some embodiments, an apparatus includes a first elongate member that defines a lumen that extends between a proximal end portion and a distal end portion of the first elongate member. A second elongate member is movably disposable within the lumen of the first elongate member. The second elongate member is flexible and includes at least one cutting member disposed on an outer surface of a distal end portion of the second elongate member. The first elongate member configured to restrain the second elongate member in a substantially linear configuration when disposed within the lumen of the first elongate member, the second elongate member being movable to a curved configuration when disposed outside of the lumen of the first elongate member. A distal end portion of the first elongate member is configured to be inserted into a portion of an anatomical structure of a patient when the distal end portion of the second elongate member is disposed within the lumen of the first elongate member. The distal end portion of the second elongate member is configured to cut tissue within the portion of the anatomical structure along a non-linear path to form a non-linear passageway within the anatomical structure when the second elongate member is moved distally relative to the first elongate member such that the distal end portion of the second elongate member extends outside of the lumen of the first elongate member and is moved to its curved configuration and the second elongate member is rotated.

In some embodiments, a method includes inserting a distal end portion of an implant into a portion of an anatomical structure within a body of a patient. The implant includes a first elongate member and a second elongate member. The first elongate member defines a lumen between a proximal end portion and a distal end portion of the first elongate member. The second elongate member is movably disposable within the lumen of the first elongate member. The second elongate member is flexible and includes at least one cutting member disposed on an outer surface of a distal end portion of the second elongate member. The distal end portion of the second elongate member being movable to a curved configuration when disposed outside the lumen of the first elongate member. Tissue is cut along a non-linear path to form a non-linear passageway within the anatomical structure by moving the second elongate member distally relative to the first elongate member and rotating the second elongate member relative to the first elongate member such that the at least one cutting member on the distal end portion of the second elongate member cuts tissue within the anatomical structure

DETAILED DESCRIPTION

The devices and methods described herein are generally directed to implants or members that can be used to support and/or stabilize anatomical structures within a body of a patient. In some embodiments, the devices and methods described herein are configured to provide support to a spine or back of a patient. In other embodiments, other portions of the body of the patient can be supported by the devices described herein.

In some embodiments, the implants or members described herein (also referred to as "apparatus" or "device") can be flexible such that the member can be inserted or implanted within a body of a patient (e.g., an anatomical structure or structures) in a curved trajectory. In some embodiments, a member described herein can be used to form or create a curved bore or passageway within an anatomical structure in which another implant can be inserted. For example, in some embodiments, a flexible cutting tool is described that can be used to form a curved bore or passageway within an anatomical structure or structure in which a flexible anchoring member or flexible fusion rod member can be inserted. In some embodiments, at least a portion of the implants described herein can be inflatable.

Figure 1:
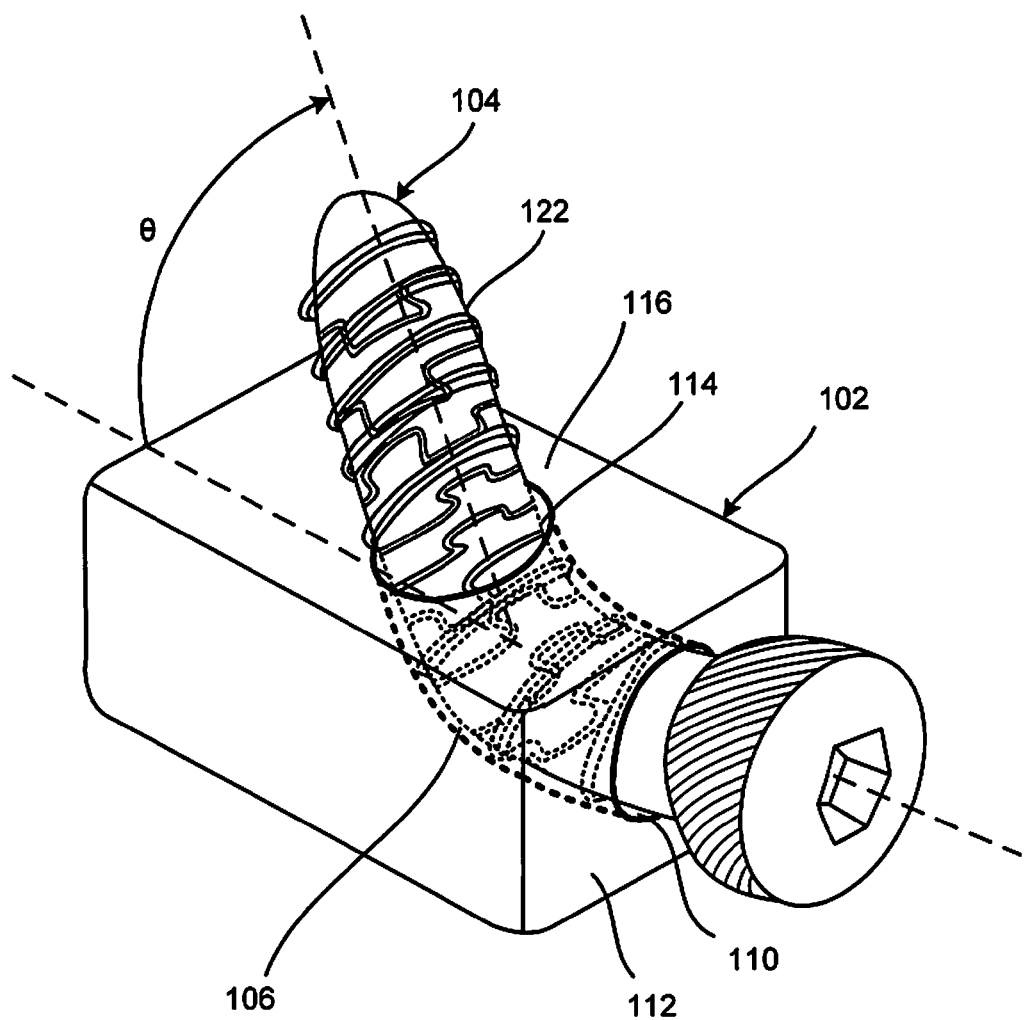
FIG. 1 is a perspective view of an implant incorporating a flexible anchoring member according to an embodiment.

FIG. 1 illustrates an implant incorporating a flexible anchoring member, according to an embodiment. The implant comprises a spacer member 102 with a flexible anchoring member 104 incorporated therein. The spacer member 102 can be implanted adjacent to or within an anatomical structure. For example, the spacer member 102 can be implanted into an intervertebral disc, or adjacent a vertebra of a patient. The spacer member 102 can be used, for example, as a support to an anatomical structure, or as a replacement for a portion of an anatomical structure. The spacer member 102 can be formed with a variety of different types of material used for such implants, such as, for example, medical grade plastic or metals. Other types of materials include cobalt chromium, stainless steel, titanium and alloys of such metals, as well as polymers such as PEEK. In some embodiments, the spacer member 102 can be formed as a solid or substantially solid component. In some embodiments, the spacer member 102 can be inflatable.

Figure 2:
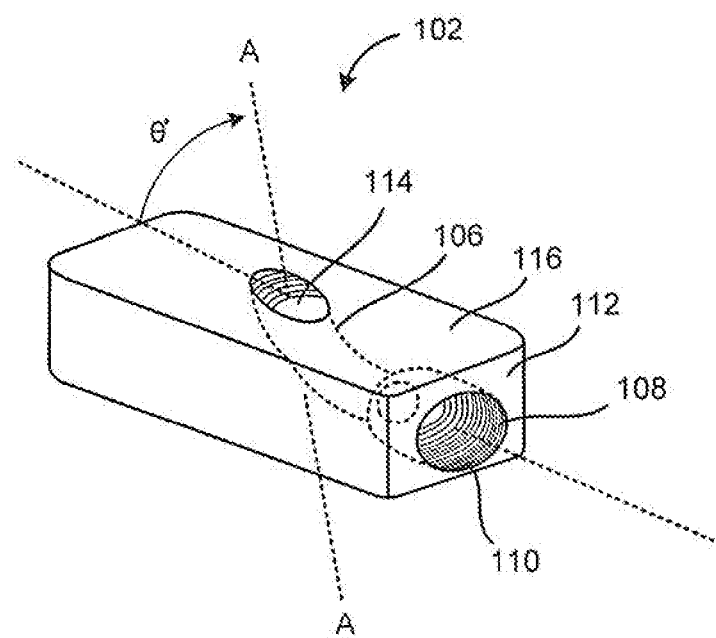
FIG. 2 is a perspective view of a spacer member of the implant of FIG. 1.

As shown, for example, in FIG. 2, the spacer member 102 defines a curved passageway or bore 106 that includes a threaded portion 108 adjacent an opening 110 defined in a sidewall 112 of the spacer 102. In some embodiments, the threaded portion 108 extends within a larger portion of the curved passageway 106. In some embodiments, the threaded portion 108 extends along the entire passageway 106. The spacer member 102 also defines an opening 114 in a top wall 116 (or any other side wall in a non-colinear trajectory) of the spacer 102. The opening 110 and the opening 114 are each in fluid communication with the curved bore 106. An axis A-A defined by the bore 106 at opening 114 of the flexible anchoring member 104 extends at an angle θ relative to a top surface of the wall 116 of the spacer member 102, as shown in FIG. 2. For example, the opening 114 can extend at an angle θ between about 5° and less than about 90°. In some embodiments, the angle θ can be, for example, 35°, 40°, 45°, 50°, 60° or 65°. Although not shown, alternatively or in addition to the openings 110 and 114, the spacer member 102 can include other openings in communication with the bore 106, such as, an opening on a bottom wall of the spacer 102 and/or an opening on any other side wall of the spacer member 102. The spacer member 102 can also include more than one curved bore.

Figure 3:
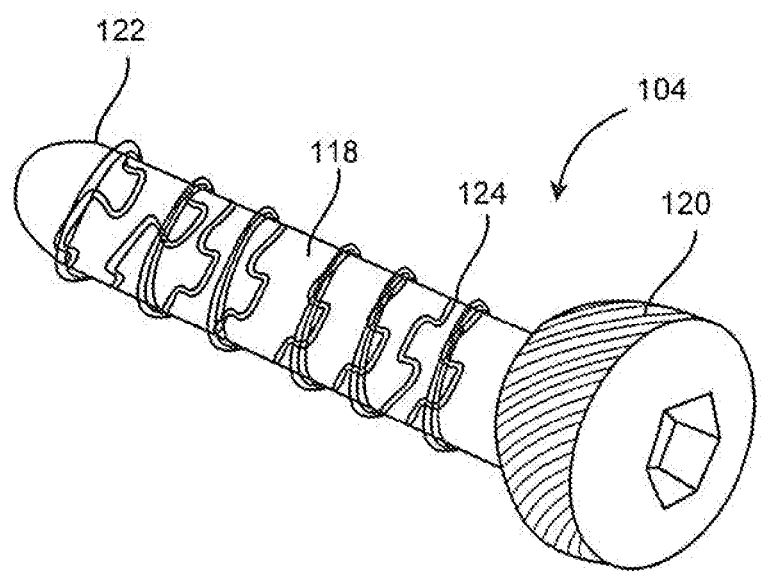
FIG. 3 is a perspective view of the anchoring member of FIG. 1.

The flexible anchoring member 104 includes a threaded portion 118 and a head portion 120 for engaging a driving tool (not shown). The threaded portion 118 includes a distal portion 122 and a proximal portion 124. The flexible anchoring member 104 can be formed with any biocompatible material, such as titanium, steel, and alloys thereof, as well as polymers such as PEEK and polyurethane. In some embodiments, the threaded portion 118 can include a helical (e.g., single or double) wire cut pattern. The flexible anchoring member 104 can have a linear or substantially linear configuration as shown, for example, in FIG. 3, or can alternatively have a zig-zag cut. The flexible anchoring member 104 can bend or flex to a variety of different curved configurations, such as the curved configuration shown in FIG. 1. In some embodiments, the flexible anchoring member 104 is flexible only along a portion of the threaded portion 118, while in other embodiments, the flexible anchoring member 104 is flexible along its entire threaded portion 118. In some embodiments, the flexible anchoring member 104 can include a number of features to aid in its flexibility, such as slits that are cut along its shaft.

The flexible anchoring member 104 can be inserted through the opening 110 of the spacer member, through the curved bore 106 and through the opening 114 of the spacer member 102. As shown in FIG. 1, a portion of the threaded portion 118 can extend out of the opening 114 of the spacer member 102 at the angle θ relative to the wall 116 of the spacer member 102.

Figure 4:
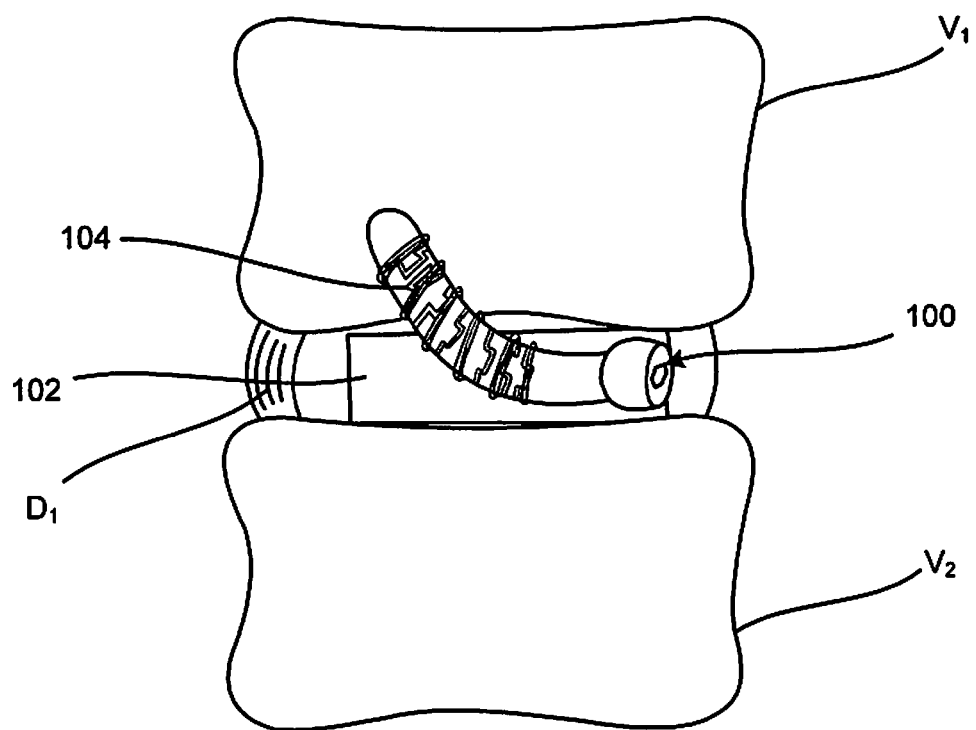
FIG. 4 is a side view of the implant of FIG. 1 coupled to a portion of a spine.

In use, the spacer member 102 can be implanted within an anatomical structure of a patient, or adjacent an anatomical structure, such as, for example, within an intervertebral disc D, or adjacent a vertebra, as shown, for example, in FIG. 4. The flexible anchoring member 104 can be inserted into the curved bore 106 of the spacer 102 and using, for example, a driver tool (not shown) can be rotated within the bore 106 such that as the distal end portion 122 of the threaded portion 118 of the flexible anchoring member 104 is moved through the opening 114 of the spacer member 102, it can be threadably inserted into a portion of an adjacent vertebra V1. The distal end portion 122 of the threaded portion 118 can engage tissue within the vertebra V1 to secure the flexible anchoring member 104 thereto. The proximal portion 124 of the threaded portion 118 of the flexible anchoring member 104 can threadably engage the threaded portion 108 within the bore 106 of the spacer member 102 to secure the flexible anchoring member 104 to the spacer member 102.

Thus, the curved bore 106 of the spacer member 102 and the flexibility of the flexible anchoring member 104 can allow the spacer member 102 to be secured or anchored to adjacent anatomical structures along a curved trajectory. The ability to curve the shaft (e.g., the threaded portion 118) of the flexible anchoring member 102 can provide access in locations that are typically not reachable without breaching a neighboring anatomical structure. In some embodiments, such a implant 100 can be desirable where anchoring of a component such as the spacer member 102 is desired and the anchoring member is not a primary load bearing component of the implant.

Figure 5:
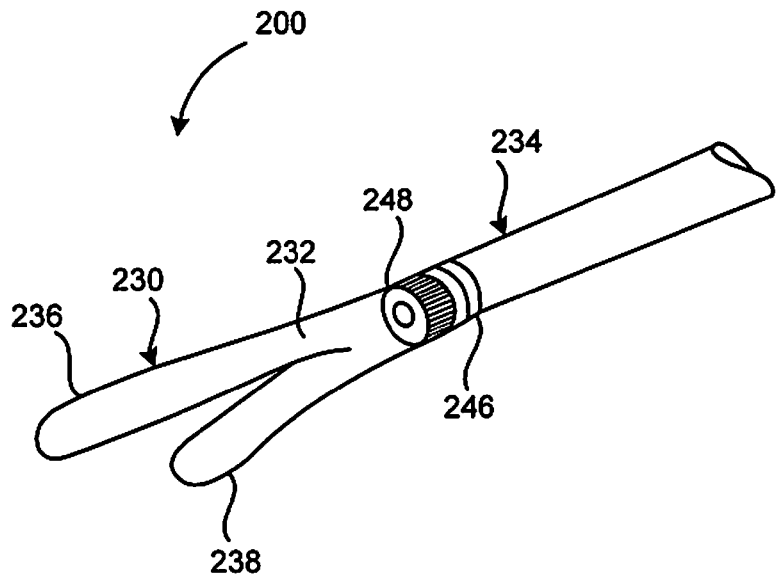
FIG. 5 is a perspective view of a portion of an expandable member accompanied by an insertion instrument according to another embodiment, shown transparent and in a partially expanded configuration.
Figure 6:
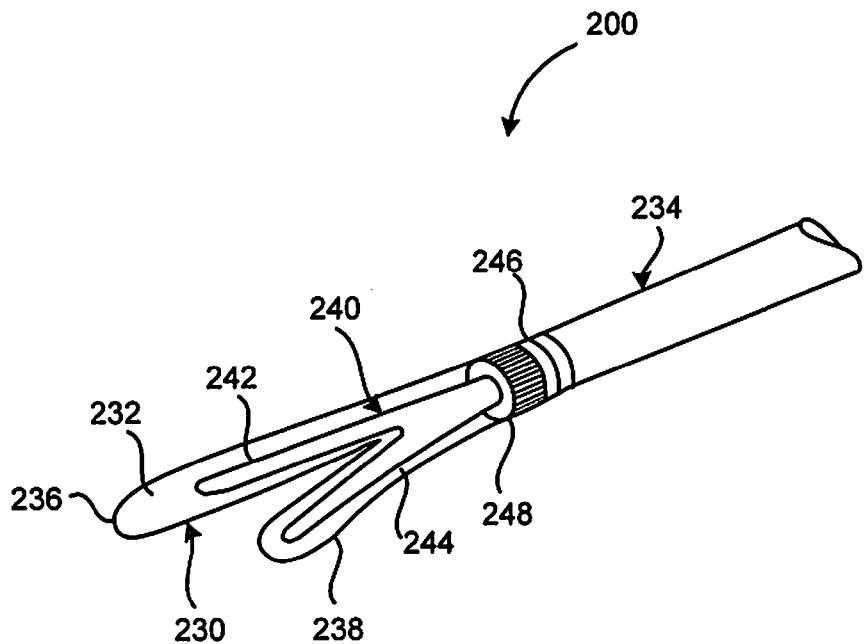
FIG. 6 is a perspective view of a portion of the expandable member of FIG. 5, shown transparent and in the partially expanded configuration.
Figure 7A:
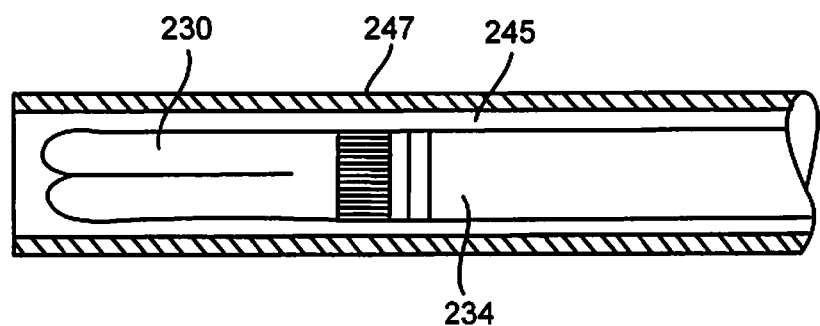
FIG. 7A is a side view partially in cross-section of a portion of the expandable member of FIG. 5, shown in a collapsed configuration within the insertion instrument.
Figure 7B:
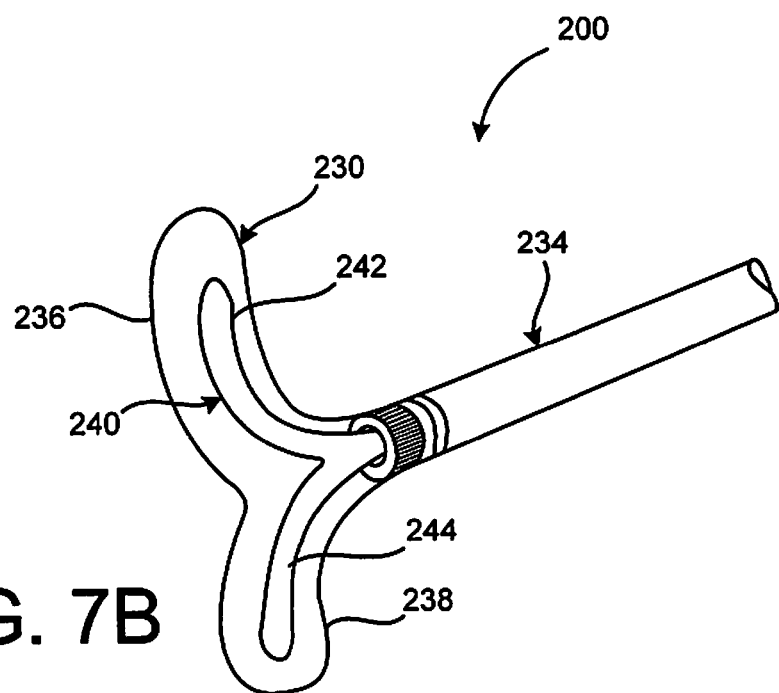
FIG. 7B is a perspective view of a portion of the expandable member of FIG. 5, shown in an expanded configuration outside of the insertion instrument.
Figure 8:
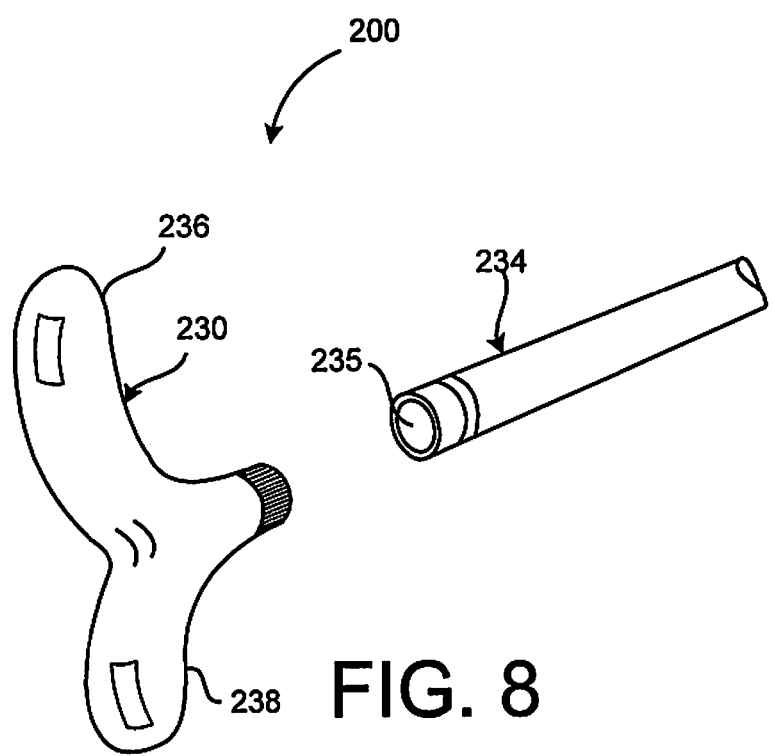
FIG. 8 is a perspective exploded view of a portion of the expandable member of FIG. 5, shown in the expanded configuration and detached from the insertion instrument.

FIGS. 5-8 illustrate an expandable member or expandable member 200 accompanied by an insertion instrument 234 according to another embodiment. The expandable member 200 can be used as an interbody fusion rod between for example, adjacent vertebra of a patient. The expandable member 200 can be inserted for example, through a pedicle of a vertebra. The expandable member 200 includes an expandable portion 230 and is accompanied by an insertion instrument 234. The expandable member includes a first portion 236 and a second portion 238, and defines an interior region 232, as shown, for example in FIGS. 5 and 6 (FIGS. 5 and 6 shown transparent for illustration purposes). The expandable member 200 can be moved between a collapsed configuration (not shown) when disposed for example, within a lumen of a cannula, and an expanded configuration, as shown in FIGS. 7B and 8 (FIGS. 5 and 6 illustrate the expandable member 200 in a partially collapsed configuration). For example, an inflation medium can be injected into the interior region 232 to move the expandable portion 230 to its expanded configuration. In some embodiments a support member 240 (described in more detail below) can help move the expandable member 200 to its expanded configuration. The expandable member 200 can be formed with, for example, a flexible and/or an elastic material. The expandable member 200 can be formed with any biocompatible material. Among the materials that can be used include silicon, polyurethane, nylon, polycarbonate urethane and other polymers. In addition, shape memory alloys such as Nitinol, elgiloy and others can also be used.

The insertion member 234 includes a distal end portion 246 that can be removably coupled to a proximal portion 248 of the expandable member 200. The insertion member 234 can include a lumen 235 that extends between a proximal end portion (not shown) and the distal end portion 246. The insertion member 234 can advantageously be used to insert the expandable member 200 into a patient's body and can also be used to inject or communicate an inflation medium, such as, for example, a curing agent, into the interior region 232 of the expandable member 200.

The expandable member 200 also includes a support member 240 (as mentioned above) that can be removably disposed within the interior region 232 of the expandable portion 230, as shown in FIG. 6. A distal end portion of the support member 240 includes a first portion 242 and a second portion 244. The first portion 242 is configured to be at least partially disposed within the first portion 236 of the expandable portion 230, and the second portion 244 is configured to be at least partially disposed within the second portion 238 of the expandable member 200. The support member 240 can also include an elongate portion (not shown) that extends to a proximal end portion (not shown) of the support member 240. In some embodiments, the support member 240 can be formed with a shape-memory material, such as, for example, Nitinol. Among the materials that can be used include silicon, polyurethane, nylon, polycarbonate urethane and other polymers. In addition, other shape memory alloys such as elgiloy can also be used.

The support member 240 is advantageously capable of being rigid enough to provide support for the expandable members, but also flexible enough to conform to different shapes. The support member 240 can have a collapsed configuration (not shown) when constrained within, for example, the lumen 235 of the insertion member 234, and can have a biased expanded configuration when not constrained, as shown in FIG. 7B (FIG. 6 illustrates the support member 240 in a partially expanded configuration). While in FIG. 7B, the support member 240 is illustrated as a single element, in other embodiments, the support member 240 can be composed of multiple elements (e.g., multiple Nitinol wires) to assist in expansion of the expandable member 200 in various directions.

The support member 240 can be used in conjunction with the inflation medium to move the expandable member 200 from its collapsed configuration to its expanded configuration. For example, the expandable member 200 can be coupled to the insertion member 234, and the expandable member 200 and the insertion member 234 can collectively be inserted through a lumen 245 of a cannula 247, as shown in FIG. 7A, to place the expandable member 200 in its collapsed configuration. In such an embodiment, the support member 240 (not shown in FIG. 7A) can be disposed in a collapsed configuration with the first portion 242 and the second portion 244 of the support member 240 disposed within the interior region 232 of the expandable member 200. With the expandable member 200 within the lumen 245 of the cannula 247, the support member 240 will be restrained in its collapsed configuration. A distal portion of the cannula 247 can then be inserted into a bore within an anatomical structure within a body of a patient. For example, one or more bores may be preformed in the anatomical structure.

When disposed at the desired location within the anatomical structure, the cannula 247 can be moved proximally and/or the expandable member 200 can be moved distally such that the expandable member 200 is moved outside of the lumen 245 of the cannula 247 and within the anatomical structure. For example, as discussed above, a bore can be preformed within the anatomical structure prior to inserting the expandable member 200 and the expandable member 200 can be disposed within the bore. At the same time, the support member 240 will be unconstrained and can begin to assume its biased expanded configuration while within the interior region 232 of the expandable member 200.

As the support member 240 is moved to its expanded configuration, the first portion 242 and the second portion 244 of the support member 240 will move apart from each other, as shown in FIG. 7B. This in turn will move the first portion 236 and the second portion 238 of the expandable member 200 away from each other. As the first portion 236 and the second portion 238 move apart from each other, they can each self-locate within a bore defined within the anatomical structure. In other words, as the expandable member 200 is expanded, the first portion 236 and the second portion 238 can find or be forced into the bores within the anatomical structure as they are expanded. After the first and second portions 236 and 238 are at least partially disposed within the bores in the anatomical structure, the support member 240 can be removed through a lumen 235 of the insertion member 234.

In some embodiments, the insertion member 234 can be used to inject or communicate an inflation medium into the interior region 232 of the expandable member 200 (e.g., via the lumen 235). The inflation medium can be for example, a curing agent that can set or harden after being injected. As the inflation medium is being injected into the interior region 232, the first portion 236 and the second portion 238 can continue to expand into the bores in the anatomical structure. When the expandable member 200 has been sufficiently expanded, the insertion member 234 can then be decoupled from the expandable member 200 (as shown in FIG. 8) and removed from the patient's body.

In some embodiments, the first portion 242 and the second portion 244 of the support member 240 can be disposed within the lumen 235 of the insertion member 234 to restrain the support member 240 in its collapsed configuration. When the expandable member 200 is disposed at the desired location within the anatomical structure, the support member 240 can be moved distally such that the first portion 242 and the second portion 244 are disposed within the interior region 232 of the expandable member 200.

In some embodiments, the expandable member 200 can be inserted into a patient's body without the use of a cannula 247 as described above. For example, the expandable member 200 can be coupled to the insertion member 234 and the support member 240 can be disposed within the lumen 235 of the insertion member 234, as discussed above. The expandable member 200 can then be inserted into an opening formed in an anatomical structure of a patient, and moved to a desired location within the anatomical structure. In such an embodiment, the expandable member 200 can maintain its collapsed configuration until the insertion member 234 injects an inflation medium into the expandable member 200 as described above, and/or until the first portion 242 and the second portion 244 of the support member 240 are moved out of the lumen 235 of the insertion member 234 and into the interior region 232 of the expandable member 200, such that the support member 240 can assume its expanded configuration as discussed above.

In some embodiments, the support member 240 can be configured to remain within the interior region 232 of the expandable member 200. In such an embodiment, the inflation medium can be injected into the interior region 232 and can surround and contact the support member 240. The support member 240 can provide additional strength to the expandable member 200 after implantation of the expandable member 200.

In some embodiments, the expandable member 200 may not include a support member 240. In such an embodiment, the inflation medium can be used to move the expandable member to its expanded configuration.

Figure 9:
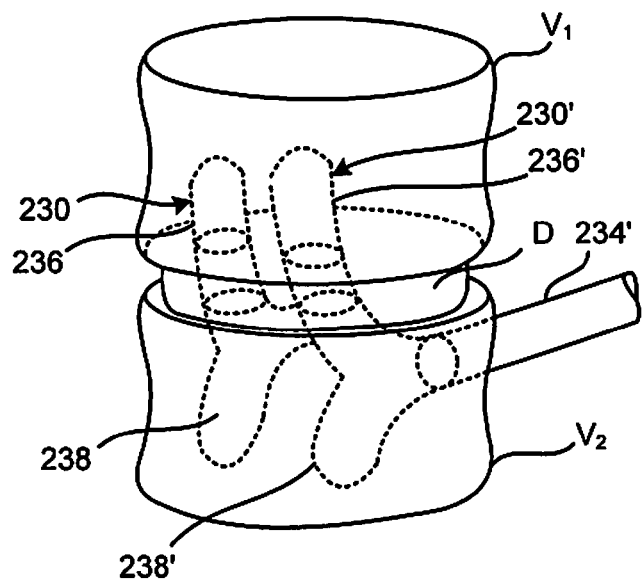
FIG. 9 is a perspective view illustrating two expandable members of FIG. 5 disposed within a portion of a spine.
Figure 10:
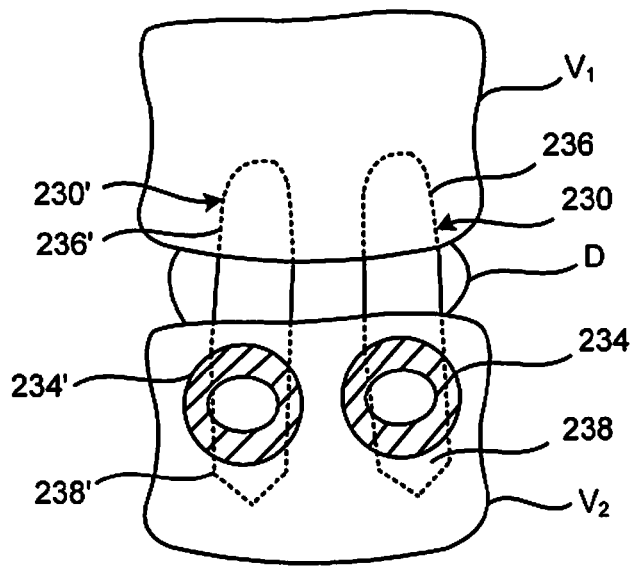
FIG. 10 is a rear view of the two expandable members and portion of a spine of FIG. 9.

FIGS. 9 and 10 illustrate the expandable member 200 and a second expandable member 200' disposed within a portion of a spine. In this example, the expandable member 200' is configured the same as the expandable member 200 described above and is therefore not described in detail here. In this example, the expandable portions 230 and 230' are each used as a fusion rod between a first vertebra V1, an intervertebral disc D and a second vertebra V2. The expandable portions 230 and 230' can each be coupled to an insertion member 234 and 234' and inserted through, for example, a pedicle of the second vertebra V2 in a similar manner as described above. The insertion member 234' can be configured the same as the insertion member 234 described above.

A first bore can be preformed within the second vertebra V2 and configured to receive the second portion 238 of the expandable members 230. A second bore can be preformed within the second vertebra V2 and configured to receive the first portion 236. In addition, a bore can be preformed through the intervertebral disc D and a bore can be preformed within the first vertebra V1 that can each be in communication with the second bore of the second vertebra V2 and can receive a portion of the first portion 236 of the expandable member 200. Thus, as the expandable member 200 is moved to its expanded configuration as described previously (e.g., via the support member and/or the inflation medium), the second portion 238 can self-locate within the first preformed bore of the second vertebra V2, and the first portion 236 can self-locate within the second preformed bore of the second vertebra V2, the preformed bore of the disc D and the preformed bore of the first vertebra V1. After the insertion member 234 has injected the inflation medium into the interior region of the expandable member 200, the insertion member 234 can be removed. The same process can be done to the expandable member 200'.

Figure 11:
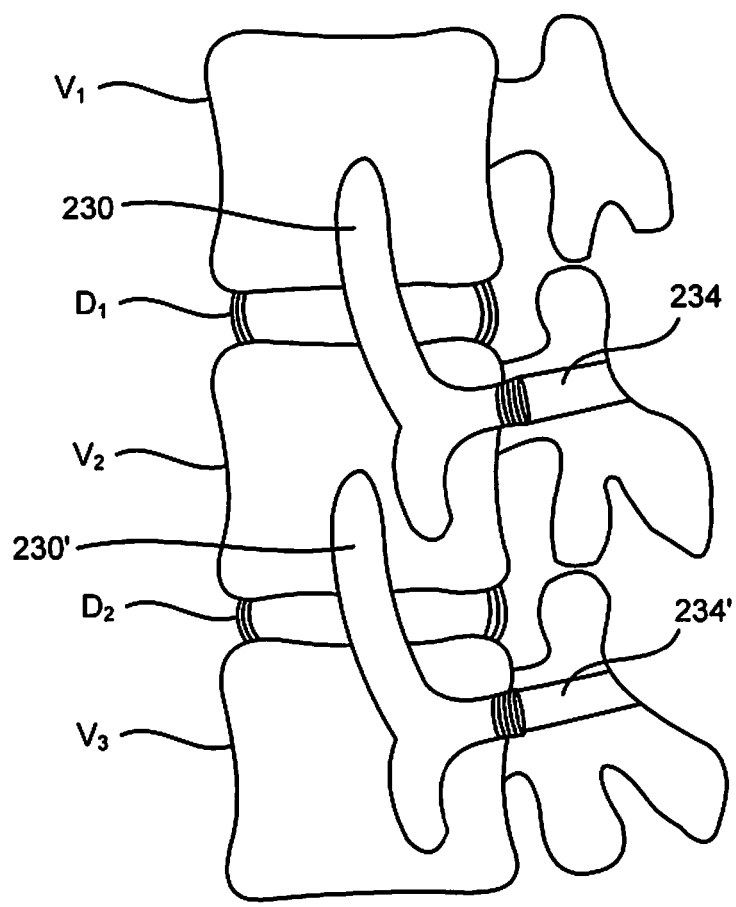
FIG. 11 is a side view of the two expandable members of FIG. 9 disposed within a portion of a spine.

FIG. 11 illustrates another example use of expandable members having expandable portions 230 and 230' as described above. In this example, the expandable portion 230 is shown being used as fusion rod between a first vertebra V1 and a second vertebra V2, and the expandable portion 230' is shown being used as a fusion rod between the second vertebra V2 and a third vertebra V3. Portions of the insertion members 234 and 234' are also illustrated. As shown in FIG. 11, the expandable portions 230, 230' can be inserted through a pedicle of the vertebra V1 and a pedicle of the vertebra V2.

Figure 12:
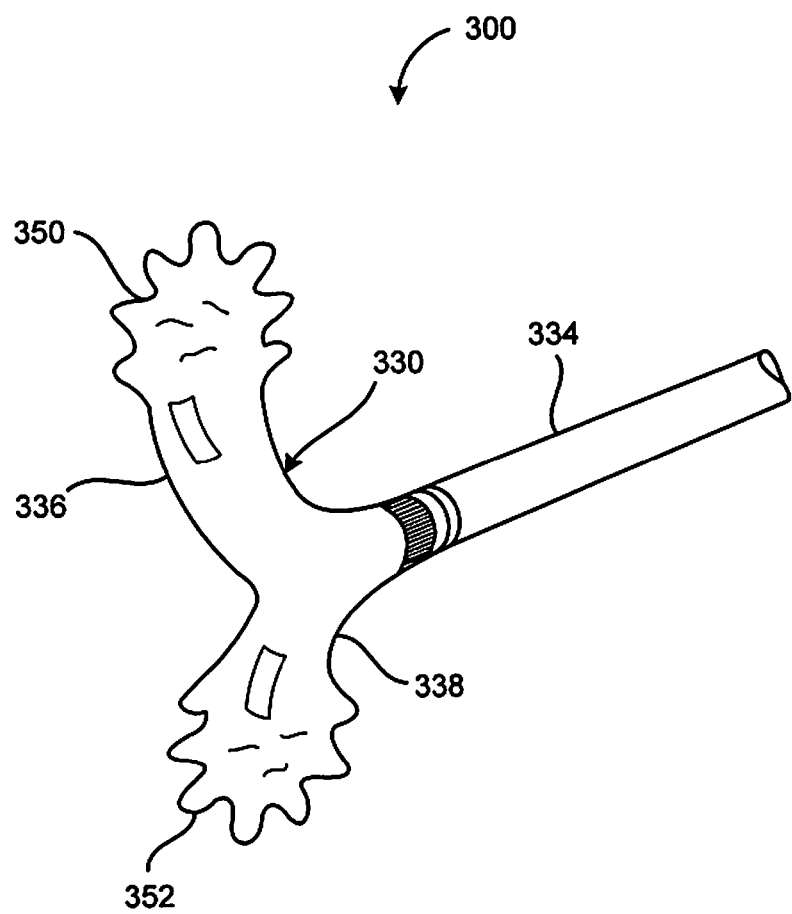
FIG. 12 is a perspective view of a portion of an expandable member according to another embodiment.

FIG. 12 is an example of an alternative embodiment of an expandable member 300 accompanied by an insertion instrument 334. In this embodiment, the expandable member 300 includes an expandable portion 330. The expandable member 300 can also include a support member (not shown) as described above for expandable member 200. The expandable member 300 can be configured similar to, and function the same as or similar to, the expandable member 200 and therefore, certain details are not repeated with respect to this embodiment.

The expandable member 300 includes a first portion 336 and a second portion 338. In this embodiment, the first portion 336 includes a first textured portion 350 and the second portion 338 includes a second textured portion 352. In some embodiments, the textured portions can comprise protrusions that extend from the surface of the expandable member. The textured portions 350 and 352 can each be used to promote engagement between the first portion 336 and the second portion 338 and the surrounding tissue within the anatomical structure in which they are being disposed. The expandable member 300 can be implanted within an anatomical structure in the same manner as described above for expandable member 200.

FIGS. 13-16 illustrate a bore forming member 400 according to another embodiment. The bore forming member 400 can be used to form a bore or passageway within an anatomical structure. For example, the bore forming member 400 can be used to form a curved or angled bore or passageway that can receive an implantable implant, such as the implants 200 and 300 described above. The bore forming member 400 includes a first elongate member 454, a second elongate member 456 and a third elongate member 460.

Figure 13:
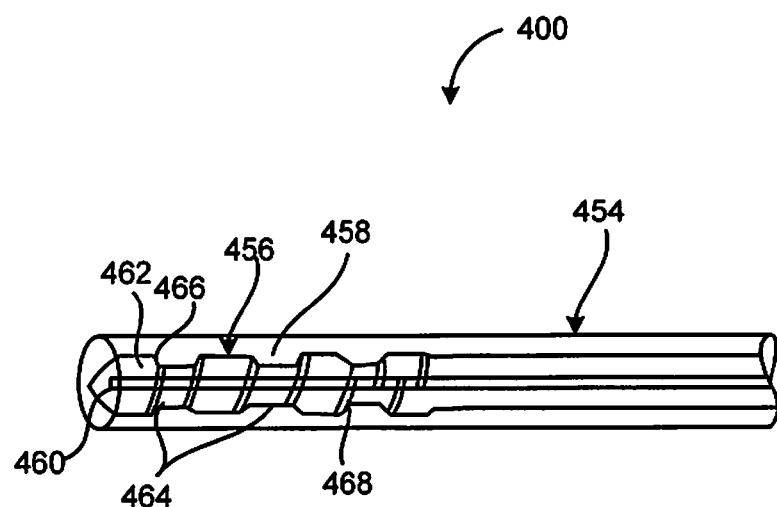
FIG. 13 is a side view of a portion of a bore-forming member according to another embodiment shown in a first configuration and with the components of the bore-forming member shown transparent.
Figure 14:
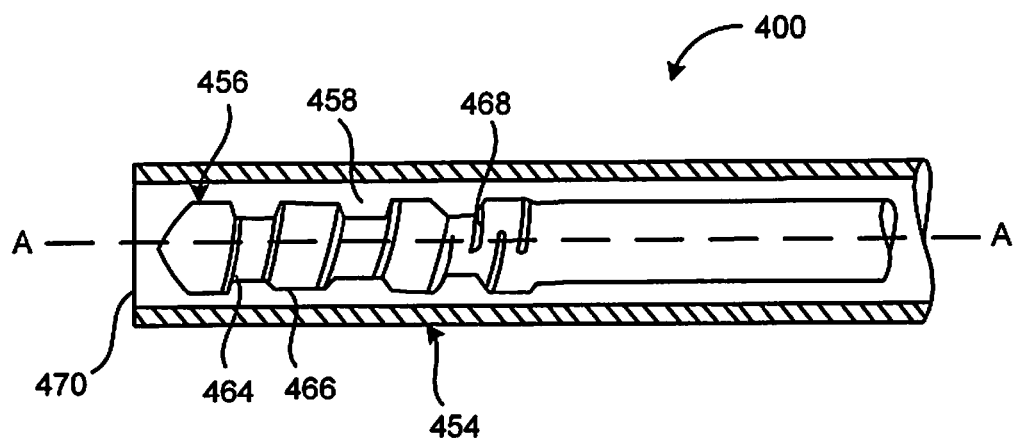
FIG. 14 is a side view shown partially in cross-section of a portion of the bore-forming member of FIG. 13 shown in the first configuration.

As shown, for example, in FIGS. 13 and 14, the second elongate member 456 can be movably received within a lumen 458 defined by the first elongate member 454. The third elongate member 460 can be received within a lumen 462 defined by the second elongate member 456. FIG. 13 shows the first elongate member 454 and the second elongate member 456 transparent for illustration purposes.

Figure 15:
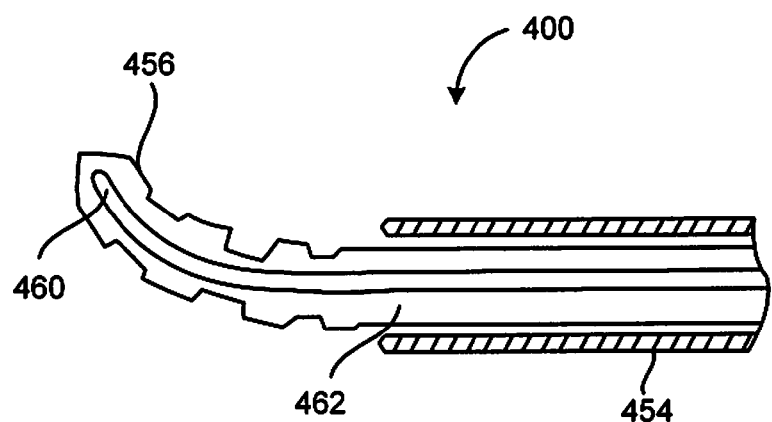
FIG. 15 is a side view shown partially in cross-section of a portion of the bore-forming member of FIG. 13 shown in a second configuration and partially transparent.
Figure 16:
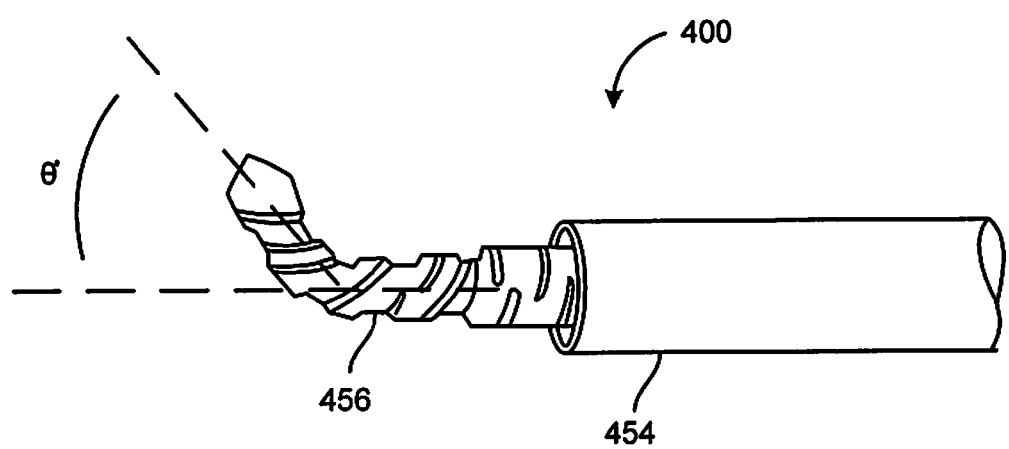
FIG. 16 is a side view of a portion of the bore-forming member of FIG. 13 shown in the second configuration.

The second elongate member 456 can be formed such that it is flexible and can be moved between a first configuration in which the second elongate member 456 is linear or substantially linear, and a second configuration in which at least a portion of the second elongate member 456 is curved. For example, when the second elongate member 456 is disposed within the lumen 458 of the first elongate member 454, as shown in FIGS. 13 and 14, the second elongate member 456 will be restrained in a substantially straight or linear configuration and define an axis A-A as shown in FIG. 14. When a distal end portion 466 of the second elongate member 456 is moved outside of the lumen 458, as shown in FIGS. 15 and 16, the distal end portion 466 of the second elongate member 456 can be moved such that the distal end portion 466 is at an angle θ relative to the axis A-A as described in more detail below. The second elongate member 456 can be formed with, for example, any biocompatible material such as stainless steel, titanium, various alloys and polymeric materials.

The second elongate member 456 can include multiple cutting portions 464 disposed on the distal end portion 466 of the second elongate member 456. In some embodiments, the second elongate member 456 may include only one cutting portion 464. In some embodiments, the second elongate member 456 can also define multiple openings 468 that are in fluid communication with the lumen 462 of the second elongate member 456. The cutting portions 464 can be used to cut (or disrupt, tear, etc.) tissue within an anatomical structure as described in more detail below. In some embodiments, the openings 468 can receive pieces of tissue that are cut by the cutting portions 464. In some embodiments, the second elongate member 456 can include less or more openings 468 than shown, and in some embodiments, the second elongate member 456 does not include openings 468.

The third elongate member 460 can be formed with a shape-memory material, such as for example, Nitinol. The third elongate member 460 can be used to move the second elongate member 456 from its first configuration (e.g., substantially linear) to its second configuration (e.g., non-linear). For example, the third elongate member 460 can have a biased pre-bent or curved shape. When disposed within the lumen 462 of the second elongate member 456 and when the second elongate member 456 is disposed with the lumen 458 of the first elongate member 454 (as shown, e.g., in FIGS. 13 and 14), the third elongate member 460 will be constrained in a substantially linear configuration. When the second elongate member 456 is moved out of the lumen 458 of the first elongate member 454, the third elongate member 460 can be allowed to assume its biased curved shape as shown in FIG. 15. As the third elongate member 460 assumes its biased curved shape, because of the flexibility of the second elongate member 456, it will in turn cause the distal end portion 466 of the second elongate member 456 to bend or curve as shown in FIGS. 15 and 16.

As discussed above, the bore forming member 400 can be used to form a non-linear bore or passageway within an anatomical structure, such as for example, a vertebra or an intervertebral disc. For example, in some embodiments, the bore forming member 400 can form a bore that has a curved trajectory. In some embodiments, the bore forming member 400 can form a bore that is angled with respect to an insertion opening of the anatomical structure. For example, the bore forming member 400 can be inserted into an anatomical structure through an opening that has a centerline axis. The bore forming member 400 can then form a bore that has a centerline axis that is at angle with respect to the centerline axis of the insertion opening into the anatomical structure.

In use, the bore forming member 400 can be inserted into an anatomical structure with the second elongate member 456 disposed within the lumen 458 of the first elongate member 454. When a distal end 470 of the first elongate member 454 is disposed at a desired location within the anatomical structure, the second elongate member 456 can be moved distally relative to the first elongate member 454 (or the first elongate member 454 can be moved proximally relative to the second elongate member 456) such that the distal end portion 466 of the second elongate member 456 is moved outside of the lumen 458 of the first elongate member 454 and within the tissue of the anatomical structure. The second elongate member 456 can be rotated when the distal end portion 466 of the second elongate member 456 is disposed outside of the lumen 458 of the first elongate member 454. The second elongate member 456 can be rotated simultaneously with the distal movement of the second elongate member 456 or after the distal movement of the second elongate member 456. As the distal end portion 466 of the second elongate member 456 is being moved outside of the lumen 458 it will also be moved to a curved or bent shape as the third elongate member 460 (disposed within the second elongate member 456) is allowed to assume its biased curved shape. Thus, the distal end portion 466 of the second elongate member 456 will be slowly moving to a curved or bent configuration while rotating within the anatomical structure. This action can allow the cutting portions 464 of the second elongate member 456 to cut tissue within the anatomical structure as the second elongate member 456 moves along a curved or angled path or trajectory within the anatomical structure. The resulting bore or passageway formed within the anatomical structure can also be curved or angled.

Figure 17:
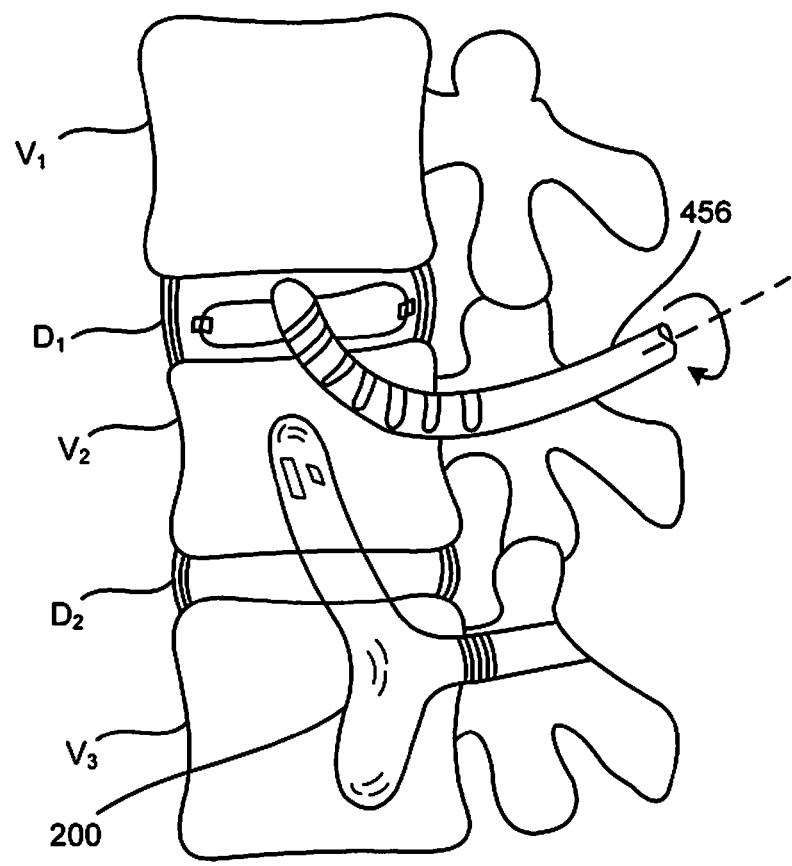
FIG. 17 is a side view of a portion of the bore-forming member of FIG. 12, shown being used within a portion of a spine, and a portion of the expandable member of FIG. 5 shown disposed within a portion of the spine.

The bore forming member 400 can be used to form a non-linear (e.g., curved or angled) bore or passageway within a single anatomical structure or within multiple anatomical structures. For example, the bore forming member 400 can be used to form a continuous curved or angled bore that extends between two or more anatomical structures. In one example, FIG. 17 illustrates the bore forming member 400 being used to form a curved bore within a vertebra V2 and also within an adjacent intervertebral disc D1. Such a curved bore can be used to implant a implant, such as the implants described herein. For example, the bore forming member 400 can preform a first bore within a vertebra V3 and a second bore that extends within the vertebra V3, into the intervertebral disc D2 and into the vertebra V2. A implant, such as the expandable member 200 (as shown in FIG. 17) can be inserted therein as described above for expandable member 200.

The bore forming member 400 can also be used to form multiple bores within the same anatomical structure. For example, the bore forming member 400 can be positioned in a first location within the anatomical structure to form a first curved or angled bore, and then be repositioned at a second location within the anatomical structure to form a second curved or angled bore.

Figure 18:
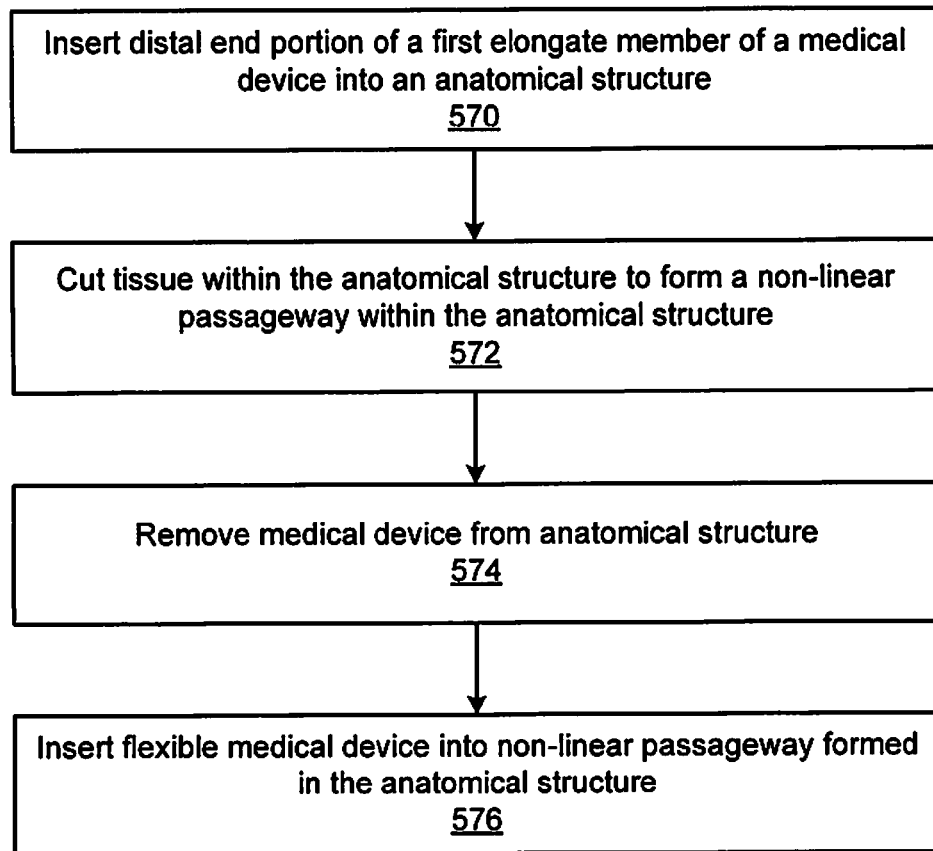
FIG. 18 is a flow chart illustrating a method forming a non-linear bore in an anatomical structure to receive a flexible member therein.

FIG. 18 illustrates a method of using a flexible member (e.g., bore forming member 400) to form a non-linear bore or passageway in an anatomical structure that can receive an implant (e.g., implants 200, 300) within the formed bore or passageway. The method includes at 570, inserting a distal end portion of a flexible member (e.g., bore forming member 400) into a portion of an anatomical structure within a body of a patient. For example, the anatomical structure can be a portion of a spine, such as a vertebra. The bore forming member can include a first elongate member (e.g., 454) that defines a lumen between a proximal end portion and a distal end portion of the first elongate member, and a second elongate member (e.g., 456) movably disposable within the lumen of the first elongate member. The second elongate member can be flexible and include at least one cutting member disposed on an outer surface of a distal end portion of the second elongate member. The distal end portion of the second elongate member can be movable to a curved configuration when disposed outside the lumen of the first elongate member. At 572, tissue can be cut along a non-linear path to form a non-linear passageway within the anatomical structure by moving the second elongate member distally relative to the first elongate member and rotating the second elongate member such that the at least one cutting member on the distal end portion of the second elongate member cuts tissue within the anatomical structure. At 574, the flexible member can be removed from the anatomical structure. At 576, a flexible implant (e.g., 200, 300) can be inserted into the non-linear passageway formed by the second elongate member.

The various components of the members or implants (e.g., 100, 200, 300, 400) described herein can be formed with any biocompatible material used for such implants. For example, each of the various components can be formed with one or more biocompatible plastics and/or one or more biocompatible metals, such as, for example, titanium and stainless steel.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments. It should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A system for fusing adjacent vertebral bodies of a spine comprising:
   an implant configured to be inserted through a pedicle of one the adjacent vertebral bodies;
   a bore forming member including:
      a first elongate member having a lumen, at least a portion of the first elongate member being generally linear;
      a second elongate member having a lumen and a tapered tip for piercing tissue, the second elongate member being received in the lumen of the first elongate member and capable of moving with respect to the first elongate member, the second elongate member having at least one cutting element disposed proximally of the tapered tip and circumferentially around an outer surface and adapted to cut tissue; and
      a third elongate member, the third elongate member being received in the lumen of the second elongate member,
   wherein the second elongate member is capable of being moved from a first configuration to a second configuration, wherein in the first configuration the second elongate member is generally linear and in the second configuration the second elongate member is generally curved,
   wherein the third elongate member is flexible and is capable of being moved from a first configuration to a second configuration, wherein in the first configuration the third elongate member is generally linear and in the second configuration the third elongate member is generally curved, and
   wherein the third elongate member is biased to the second configuration such that movement of the third elongate member outside of the first elongate member causes the third elongate member to move from the first configuration to the second configuration and causes a corresponding movement of the second elongate member,
   wherein the at least one cutting element of the second elongate member is sized and adapted to create a bore having an insertion opening in tissue for receiving the implant, wherein the implant is an interbody fusion rod configured to be received in the bore to fuse the adjacent vertebral bodies,
   wherein the bore has a generally constant diameter and a first portion having a first curvilinear trajectory and a second portion having a second curvilinear trajectory,
   wherein the first curvilinear trajectory of the bore extends along a first axis that is angled with respect to an axis of the bore at the insertion opening,
   wherein the second curvilinear trajectory of the bore extends along a second axis that is angled with respect to the axis of the bore at the insertion opening and transverse to the first axis, and
   wherein the implant is adapted to substantially fill the first and second portions to substantially plug the bore.

2. The system of claim 1, wherein when the second elongate member is disposed in the lumen of the first elongate member, the second elongate member is in the first configuration.

3. The system of claim 1, wherein when a distal portion of the second elongate member is disposed outside the lumen of the first elongate member, the distal portion of the second elongate member is generally curved.

4. The system of claim 3, wherein the curvature of the distal end of the second elongate member is at an angle of generally between 5 degrees and 90 degrees from a longitudinal axis of the first elongate member.

5. The system of claim 1, wherein the second elongate member is formed from a biocompatible material including stainless steel, titanium, polymers or alloys.

6. The system of claim 1, wherein the second elongate member includes a plurality of cutting elements disposed on a distal end portion.

7. The system of claim 6, wherein the distal end of the second elongate member includes a tip portion, the tip portion having a generally frustoconical shape.

8. The system of claim 1, wherein the third elongate member is formed with a shape memory alloy.

9. The system of claim 1, wherein the third elongate member is used to move the second elongate member from the first configuration to the second configuration.

10. The system of claim 1, wherein the at least one cutting element of the second elongate member includes a plurality of cutting elements each disposed proximally of the tapered tip and circumferentially around an outer surface.

11. The system of claim 10, wherein two adjacent cutting elements form a circumferential recess.

12. The system of claim 1, wherein the implant is an expandable implant.

* * * * *